United States Patent [19]

Vanderveen et al.

[11] Patent Number: 4,818,442

[45] Date of Patent: Apr. 4, 1989

[54] DISPROPORTIONATION PROCESS

[75] Inventors: John W. Vanderveen; Dennis S. Banasiak, both of Bartlesville, Okla.

[73] Assignee: Phillips Petroleum Company, Bartlesville, Okla.

[21] Appl. No.: 658,926

[22] Filed: Oct. 9, 1984

[51] Int. Cl.$^4$ .................... C07C 67/475; C07C 41/30; C07C 6/04; C07C 17/26

[52] U.S. Cl. ................ 260/405.5; 260/404; 260/408; 260/410.9 R; 556/465; 556/466; 556/482; 556/469; 570/189; 570/218; 570/237; 568/687; 560/190; 560/261; 560/262; 585/643; 585/647

[58] Field of Search ............ 560/261, 262, 190; 260/410.9 R, 405.5, 408, 404; 570/189, 218, 237; 585/647, 643; 568/687; 556/465, 466, 482, 469

[56] References Cited

U.S. PATENT DOCUMENTS 2,923,725  2/1960  Nowlin et al. ............... 260/448
3,974,196  8/1976  Nakamura et al. .......... 260/410.9 R
4,269,780  5/1981  Banasiak ....................... 260/405

OTHER PUBLICATIONS

Synthesis 12/77, pp. 817–836, "Insect Pheromones; I. Synthesis of Achiral Components of Insect Pheromones," Renzo Rossi.

*Primary Examiner*—Vivian Garner
*Attorney, Agent, or Firm*—Williams, Phillips & Umphlett

[57] ABSTRACT

A process for the disproportionation of olefins comprising contacting said olefins under suitable reaction conditions with a neutral-carbene complex catalyst and then using anhydrous ammonia to effect separation of the catalyst and the organic products.

8 Claims, No Drawings

DISPROPORTIONATION PROCESS

The present invention relates to the disproportionation of olefins. In a more specific aspect the present invention relates to olefin disproportionation employing a neutral carbene catalyst.

The disproportionation or metathesis of olefins is a reaction in which one or more olefinic compounds are transformed into other olefins of different molecular weights. The disproportionation of an olefin to produce one olefin of a higher molecular weight and one olefin of a lower molecular weight can also be referred to as a self-disproportionation. For example, propene can be disproportionated to ethylene and cis- and trans-2-butene. Another type of disproportionation involves the codisproportionation of two different olefins to form still other olefins. For example, the reaction of one molecule of 2-butene with one molecule of 3-hexene can produce two molecules of 2-pentene.

Several catalyst systems have been proposed for the disproportionation of olefins. A particularly desirable type of catalyst system involves the use of a homogeneous catalyst containing a neutral carbene-metal complex. Some examples of such catalysts are disclosed in U.S. Pat. No. 4,247,417; U.S. Pat. No. 4,248,738; and U.S. Pat. No. 4,269,780 the disclosures of which are incorporated herein by reference. Those patents disclose that if one wishes to remove the catalyst from the product of the disproportionation reaction such can be done by addition dilute aqueous ammonium to the reaction product to decompose and precipitate the catalyst, filtering, extracting the water, and purifying the organic products such as by distillation. Typically it has also been necessary to contact the organic product with a drying agent to remove the water.

An object of the present invention is to provide an improved technique for separating the catalyst from the reaction product of such disproportionation product.

Other objects, features and advantages of the present invention will appear more fully from the following description.

SUMMARY OF THE INVENTION

In accordance with the present invention olefins are disproportionated using a catalyst comprising a neutral carbene-metal complex and the catalyst is removed from the reaction product by contacting with anhydrous ammonia to obtain a solid which is separated from the liquid.

DETAILED DESCRIPTION

The carbene complex component of the catalyst system of this invention is a neutral, i.e., non-ionic, carbene complex having the general formula I

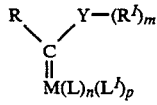   (I)

wherein R is an aryl or substituted aryl radical containing from 6 to about 30 carbon atoms per radical and with the aryl substituents being one or more or a mixture selected from a group consisting of halides, alkoxides, and alkyl radicals containing 1 to 20 carbon atoms per radical, $R^I$ is selected from a group consisting of alkyl, cycloalkyl, aryl, substituted aryl, trialkylsilyl, or triarylsilyl radicals containing from 1 to 30 carbon atoms per radical with the aryl substituents being the same as for R described above, Y is 0, Se, S, N, or P, m is 1 when Y is 0, Se, or S and m is 2 when Y is N or P, M is tungsten or rhenium, each L is a neutral ligand individually selected from the group consisting of CO, NO, $PF_3$, $PCl_3$, and pyridine, $L^I$ is cyclopentadienyl or allyl, and p is 0 or 1, and when p is 0 n is 5 and when p is 1 n is 2. Mixtures of ligand L can be used if desired. Specific examples of neutral carbene complexes include (methoxyphenylcarbene)pentacarbonyltungsten(O), (p-chlorophenylmethoxycarbene)pentacarbonyltungsten(O), p-methylphenylmethoxycarbene)-pentacarbonyltungsten(O), (p-methoxyphenylmethoxycarbene)pentacarbonyltungsten(O), (phenoxyphenylcarbene)pentacarbonyltungsten(O), (cyclohexyloxyphenylcarbene)pentacarbonyltungsten(O), (butoxyphenylcarbene)pentacarbonyltungsten(O), (octyloxyphenylcarbene)pentacarbonyltungsten(O), (hexadecyloxyphenylcarbene)pentacarbonyltungsten(O), (eicosyloxyphenylcarbene)pentacarbonyltungsten(O), (phenyltrimethylsiloxycarbene)pentacarbonyltungsten(O), (phenyltriphenylsiloxycarbene)pentacarbonyltungsten(O), (methylthiophenylcarbene)pentacarbonyltungsten(O), (dimethylaminophenylcarbene)pentacarbonyltungsten(O), (methoxyphenylcarbene)pentanitrosyltungsten(O) and corresponding rhenium carbenes. Mixtures of carbene complexes can be used if desired.

The presently preferred catalysts are those of formula I wherein R is a phenyl radical, Y is oxygen, $R^I$ is an alkyl radical containing 1 to about 10 carbon atoms per radical, m is 1, L is CO or No, n is 5, and p is 0.

For reasons of ease of preparation and reactivity, the currently most preferred carbene complex is

   (II)

wherein $C_6H_5$ is phenyl group.

The carbene complexes can be prepared by any of several published procedures, for example: D. J. Cardin, et al. Chem. Rev., 72, 545 (1972). D. J. Cardin, et al, Chem. Soc. Rev., 2, 99 (1973). C. P. Casey, in "Transition Metal Organometallic in Organic Synthesis", Vol. 1, H. Alper, Ed., Academic Press, 1976, pp 189-233. "Inorganic Synthetis" Vol. 17, 95-99 (1979). In a typical preparation, carbene complex II is prepared by reacting tungsten hexacarbonyl with phenyllithium and then with the trimethyloxonium tetrafluoroborate.

The preferred caralysts are those in which the catalyst comprises the neutral carbene and other catalyst components of the type disclosed in the above-mentioned patents.

An especially preferred type of catalyst is the catalyst comprising the metal carbene and a tetrahalide of germanium, tin, or lead; and silicon tetrahalide wherein in the carbene complex R is selected from a group consisting of alkyl, cycloalkyl, aryl, or substituted aryl radicals containing from 1 to about 30 carbon atoms per radical and the aryl substituents being one or more or a mixture selected from a group consisting of halides and alkoxides or alkyl radicals containing 1 to 20 carbon atoms per radical, and the like, with the limitation that R should not be alkyl or cycloalkyl when a functional olefin is used, $R^I$ is selected from a group consisting of alkyl, cycloalkyl, aryl, substituted aryl, trialkylsilyl, or triarylsilyl radicals containing from 1 to 30 carbon atoms per radical with the aryl substituents being the same as described above for R with the limitation that R and $R^I$ are not both aryl or substituted aryl when Y is S and functional olefins are used, Y is O or S, m is 1, M is tungsten or rhenium, L is CO or NO, p is 0 when n is 5 or p is 1 and n is 2, and $L^I$ is cyclopentadienyl.

The germanium, tin, and lead tetrahalides employed in this embodiment are selected from the group consisting of tin tetrachloride, tin tetrabromide, germanium tetrachloride, germanium tetrabromide, lead tetrachloride, and lead tetrabromide. For reasons of high reactivity, the presently preferred metal compound components are tin tetrachloride and germanium tetrachloride.

The silicon tetrahalide is selected from silicon tetrachloride and silicon tetrabromide.

The molar ratio of the germanium, tin, or lead tetrahalide to the carbene complex in this embodiment is broadly from about 1/1 to about 500/1 and preferably from about 5/1 to about 100/1. The molar ratio of silicon tetrahalide to the germanium, tin, or tetrahalide is broadly from about 0.1/1 to about 200/1 and preferably about 0.5/1 to about 50/1.

REACTION CONDITIONS

The amount of catalyst employed in the process of this invention can be expressed in terms of the molar ratio of olefin to carbene complex component. Generally, the molar ratio of the total stoichiometric amount of olefinic reactant to carbene complex component is in the range of about 1/1 to about 500/1 and preferably from about 50/1 to about 2000/1. The term "total stoichiometric amount" is used herein to denote the moles of reactant that could theoretically react so as to distinguish from cases when two or more olefins are employed and one or more is used in a greater amount than will react. Thus, the amount of catalyst is generally based upon the amount of reactive olefins and not on excess olefin.

The disproportionation reaction of this invention can be carried out at temperatures between about 35° C. and about 200° C. While lower temperatures can be used, the reaction rates are generally too low to be of interest. Temperatures above 200° C. can be used, but excess decomposition of the reaction components can occur. The preferred reaction temperatures are from about 50° C. to about 125° C.

The pressure during the disproportionation reaction can be from about atmospheric to about 5000 psig (34,470 kiloPascals kPa). Preferably, the pressure is from about atmospheric to about 1000 psig (6894 kPa).

The disproportionation reaction can be carried out in the presence of diluents such as saturated hydrocarbons, e.g., hexane, octane, cyclohexane, aromatic hydrocarbons, e.g., benzene, toluene, or halogenated compounds, e.g., chlorobenzene, chloroform, methylene chloride, bromoform, and the like.

Diluents containing aromatic groups, e.g., chlorobenzene, have been found to sometimes undergo alkylation when utilized with Group VIb metal halides, e.g., $WCl_6$, at the higher metal compound component levels. This can of course result in decreased yields and therefore may be viewed as undesirable. Also the use of saturated hydrocarbons, e.g., hexane, as diluents with catalyst systems containing metal compounds from Group Vb frequently results in decreased yields and are thus less desirable. This indicates that the diluent is not a completely inert component of the reaction system and attention must be paid to the diluent used for any specific combination of reaction ingredients. In embodiment C, the carbon tetrachloride component of the catalyst system can be used, especially in the upper portion of the concentration range, as a diluent.

The amount of diluent can be expressed as a volume ratio of diluent to the olefin. Suitable volume ratios of diluent to olefin can be from about 0/1 to about 500/1 and preferably from about 1/1 to about 300/1.

The presence of oxygen and water has been found to be deleterious to the disproportionation reaction and should be substantially avoided during the reaction. Inert gases such as nitrogen or helium can be used to maintain a dry, inert atmosphere during the reaction.

The metal compounds used as components of the catalyst system should be pure, free of oxygen or water, and free of any hydrolysis products. In general, the yield of disproportionatin product decreases as the metal compound purity decreases.

The functional olefins used in the disproportionation reaction should be dry and free of polar materials such as carboxylic acids or alcohols. A purification step to remove impurities by such methods as filtering through silica gel and storing over molecular sieves or distilling from suitable drying agents is beneficial.

The reaction time period depends on the reaction temperature and pressure as well as on the nature of the particular catalyst system and olefinic reactant used. The reaction time is generally from about 30 minutes to 14 days. Preferably the reaction time is from about 2 to about 120 hours. Olefins containing functional groups frequently undergo disproportionation reactions slower than non-functional olefins and longer reaction times may be appropriate.

Suitable olefin reactants can be readily discovered by routine experimentation. Generally the process involves the contacting of two olefinic reactants, which may be the same or different olefins, with a catalyst system of the type described above. Typically, at least one of the olefinic reactants contains 3 to 30 carbon atoms per molecule and one or more non-conjugated carbon-carbon double bonds.

Generally, at least one of the olefinic reactants contains one or two non-conjugated carbon-carbon double bonds and is an acyclic olefin represented by the formula:

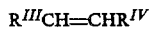

wherein $R^{III}$ and $R^{IV}$ are independently selected from a group consisting of hydrogen, alkyl radicals, alkaryl radicals, and alkenyl radicals with each of the radicals containing from 1 to about 18 carbon atoms per radical or a monocyclic olefin represented by the formula:

wherein $R^V$ is an alkylene or alkenylene radical containing from 5 to about 16 carbon atoms and wherein each of the radicals $R^{III}$, $R^{IV}$, and $R^V$ can contain one or more or a mixture of functional groups selected from a group consisting of esters, ethers, halides, e.g., fluorine, chlorine, bromine, or iodine, trisubstituted silyloxy($-OSiR^{VI}_3$), trisubstituted silyl($-SiR^{VI}_3$), and ammonium salts ($-N^+R^{VII}_3X^-$) wherein $R^{VI}$ is an alkyl, aryl, or substituted aryl radical containing from 1 to about 20 carbon atoms per radical with the aryl substituents being halides, alkoxides, or alkyl radicals, each $R^{VII}$ is hydrogen or an alkyl radical with at least one alkyl radical being required and containing from 1 to 10 carbon atoms per radical, and X is chloride, bromide, or iodide.

The first four of these functional groups, i.e., esters, ethers, halides, and trisubstituted silyloxy, must be located at least two saturated carbon atoms from the olefinic carbons, i.e., the functional group is on a carbon atom that is separated from the olefinic carbons by at least one saturated carbon atom. The last two functional groups must be located at least one carbon atom from the olefinic carbons.

The olefinic double bond in an unsaturated ester can be located on either the alcohol or on the acid portion form which the ester was formally prepared. When an aryl group is present in the olefin, the aryl and olefinic groups should not be conjugated.

Examples of suitable acyclic olefinic reactants include propene, 1-butene, 1-pentene, 2-pentene, 1-hexane, 2-hexane, 1-octene, 2-octene, 4-methyl-1-heptene, 1-decene, 2-decene, 6-dodecene, 1 tetracene, 1-eicosene, 1,4-hexadiene, 4-phenyl-1-butene, 4-phenyl-1 ocetene, 4-pentene-1-yl acetate, 4-chloro-1-pentene, 5-chloro-1-pentene, methyl oleate, methyl 10-undecenoate, ethyl oleyl ether, 3-butenyl methyl ether, 3-pentenyl propyl ether, methyl 4-hexenoate, ethyl 5 hexenonate, 4-bromo-1-butene, 4-iodo-1-butene, 3-buten-1 oxy-trimethylsilane, 3-propen-1-yltrimethylsilane, and 3-butene-1 yltrimethylammonium chloride. Examples of suitable monocyclic olefins include cycloheptene, cyclooctene, cyclononene, cyclotetradecene, 4 chloro-1-cyclooctene, 1,5-cyclodedecadiene, and 1,6-cyclodecadiene.

When two different olefinic reactants are utilized in the disproportionation, one of the olefins must be an olefin as described above and the other olefin can be either another olefin as described above or can be ethylene, a monocyclic monoolefin containing 4, 5, or 6 carbons in the ring, e.g., cyclobutene, cyclopentene, cyclohexene, or polycyclic mono- or diolefins. Examples of suitable polycyclic olefins include bicyclo[2.2.2]oct-2-ene, bicyclo[2.2.2]oct-2,5-diene, bicyclo[2.2.1]hept-ene, and bicyclo[3.3.0]oct-2-ene.

When two different olefinic reactants are employed in the disproportionation process, the molar ratio of one olefinic reactant to the other olefinic reactant is not critical, and, although about equimolar quantities are normally employed, up to as much as a 10-fold excess, preferably up to a 2-fold excess of one olefinic reactant can be employed.

The optimum amount of anhydrous ammonia needed to precipitate the catalyst can be readily determined by routine experimentation. The temperature for the precipitation is not considered to be critical. Obviously however temperatures should be employed which would not have an adverse effect upon the desired products of the disproportionation. Typically, temperatures in the range of about 20° C. to about 80° C. would be used, more preferably temperatures in the range of 25° C. to 60° C. would be used.

A further understanding of the present invention and its advantages will be provided by the following example.

EXAMPLE

A 1 liter autoclave was charged with 102 grams (1.76 moles) of 1-butene, 200 ml (0.88 moles) of 9-decenyl acetate, 0.002 mole of 1 methoxyphenylcarbene) pentacarbonyl tungsten (O), 0.060 moles SnCl$_4$, and 0.080 moles SiCl$_4$, in 200 ml of chlorobenzene. The autoclave was sealed and the reaction mixture heated up to about 107° C. and maintained at a temperature in the range of 94° to 107° C. with stirring for about 2½ hours. Then the autoclave was vented and the mixture allowed to cool to about 50° c. Anhydrous ammonia was then added to the mixture. The pressure increased from 5 psig to 105 psig. After the pressure had dropped down to about 10 psig another portion of anhydrous ammonia was added. The temperature was about 56° C. The pressure increased to about 108 psig. About 30 minutes after the first ammonia addition the reactor was opened and the reaction mixture was removed from the reactor. The reaction mixture was yellow, contained a white precipitate, and evolved some gas. GC analysis showed that self and cross metathesis had occurred and that there was very little else in the way of other organic reaction products. The yield of 9-dodecenyl acetate was 10.9% and the yield of 1,18-diacetoxy-9-octadecene was 8%. The trans to cis ratio of the 9-dodecenyl acetate was about 2/1. The yield of the self and cross metathesis products was substantially the same as that obtained using a comparable reaction which differed mainly only in that no anhydrous ammonia was employed.

Thus the anhydrous ammonia allows the precipitation of the catalyst without any adverse effect upon the methathesis reaction products. It allows one to dispense with the use of extraction and drying agents that are generally used if aqueous ammonium is used in the workup.

What is claimed is:

1. A process for the disproportionation of olefins comprising (1) contacting said olefins under suitable reaction conditions with a catalyst comprising a neutral carbene-metal complex having the general formula

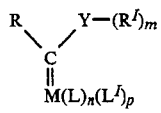

wherein R is selected from the group consisting of alkyl or cycloalkyl radicals containing 1 to 10 carbon atoms per radical, aryl or substituted aryl radicals containing 6 to 30 carbon atoms per radical wherein the substituted aryl radicals can have one or more substitutents each of which can be the same or different and selected from the group consisting of halides, alkoxides, and alkyl radicals containing 1 to 20 carbon atoms per radical; wherein $R^I$ is selected from the group consisting of alkyl, cycloalkyl, aryl, substituted aryl, triarylsilyl, and trialkylsilyl radicals containing 1 to 30 carbon atoms per radical and wherein the aryl substituents are as described for R; M can be Cr, when said metal compound component contains Ti, or M can be W or Re; Y is O, Se, S, N, or P, each L is a neutral ligand individually selected from CO, NO, PR$_3^I$, PCl$_3$, RF$_3$, and pyridine, where $R^I$ is as defined above, and $L^I$ is cyclopentadienyl; p is 0 or 1; n is 5 when p is 0 or 2 when p is 1; and m is 2 when Y is N or P and 1 when Y is O, Se, or S, and (2) removing the catalyst from the reaction product by contacting said reaction product with anhydrous ammonia to obtain a solid which is separated from the liquid.

2. A process according to claim 1 wherein the liquid remaining after the solid is removed is subjected to distillation in order to obtain separation of the various components in the liquid.

3. A process according to claim 1 wherein said catalyst comprises $SnCl_4$ and $SiCl_4$.

4. A process according to claim 3 wherein said catalyst comprises (methoxyphenylcarbene) pentacarbonyl tungsten (O).

5. A process according to claim 3 wherein said olefin reactant includes an olefin containing a functional group selected from ester, ether, and halide functionality.

6. A process according to claim 1 wherein said catalyst comprises (methoxyphenylcarbene) pentacarbonyl tungsten (O).

7. A process according to claim 6 wherein said olefin reactant includes an olefin containing a functional group selected from ester, ether, and halide functionality.

8. A process according to claim 1 wherein said olefin reactant includes an olefin containing a functional group selected from ester, ether, and halide functionality.

* * * * *